(12) United States Patent
Krauss et al.

(10) Patent No.: US 10,743,924 B2
(45) Date of Patent: Aug. 18, 2020

(54) BONE REDUCTION AND IMPLANT HOLDING INSTRUMENT

(71) Applicant: Stryker European Holdings I, LLC, Kalamazoo, MI (US)

(72) Inventors: Antina Krauss, Waldkirch (DE); Matthias Leyendecker, Freiburg (DE); Martin Knape, March-Hugstetter (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 531 days.

(21) Appl. No.: 15/414,108

(22) Filed: Jan. 24, 2017

(65) Prior Publication Data

US 2017/0209192 A1  Jul. 27, 2017

Related U.S. Application Data

(60) Provisional application No. 62/286,671, filed on Jan. 25, 2016.

(51) Int. Cl.
| *A61B 17/80* | (2006.01) |
| *A61B 17/17* | (2006.01) |
| *A61B 17/88* | (2006.01) |
| A61B 17/00 | (2006.01) |

(52) U.S. Cl.
CPC ........ *A61B 17/808* (2013.01); *A61B 17/1728* (2013.01); *A61B 17/8866* (2013.01); *A61B 2017/0046* (2013.01)

(58) Field of Classification Search
CPC ........................... A61B 17/808; A61B 17/1728
See application file for complete search history.

(56) References Cited

U.S. PATENT DOCUMENTS

| 2,291,413 | A |   | 7/1942 | Siebrandt |
| 2,583,896 | A | * | 1/1952 | Siebrandt ............. A61B 17/808 606/86 R |
| 3,145,388 | A | * | 8/1964 | Carpinella ........... A41H 37/006 227/15 |
| 5,129,908 | A |   | 7/1992 | Petersen |
| 5,697,933 | A |   | 12/1997 | Gundlapalli et al. |
| 6,579,296 | B1 | * | 6/2003 | Macey ................ A61B 17/808 606/86 R |

(Continued)

FOREIGN PATENT DOCUMENTS

| CH | 708407 B1 | 2/2015 |
| WO | 2012161977 | 11/2012 |
| WO | 2015049558 A2 | 4/2015 |

*Primary Examiner* — Nicholas W Woodall
(74) *Attorney, Agent, or Firm* — Lerner, David, Littenberg, Krumholz & Mentlik, LLP (57) ABSTRACT

A bone reduction instrument includes first and second members moveably coupled to each other such that ends of the first and second members are positionable in first and second positions. In the second position the first and second members are closer to each other than in the first position. The instrument also includes a support member disposed at the end of the first member and includes a plate retaining portion extending from the first member in a direction toward the second member. The plate retaining portion includes wall portions that define a space therebetween configured to receive a bone plate so that the bone plate is held between the wall portions when the bone plate is disposed within the space.

14 Claims, 9 Drawing Sheets

(56) References Cited

U.S. PATENT DOCUMENTS

| | | | |
|---|---|---|---|
| 8,313,492 B2 * | 11/2012 | Wong | A61B 17/1703 606/96 |
| 2011/0152953 A1 | 6/2011 | Link | |
| 2014/0031882 A1 | 1/2014 | Schmuck et al. | |

* cited by examiner

BONE REDUCTION AND IMPLANT HOLDING INSTRUMENT

CROSS-REFERENCE TO RELATED APPLICATION

The present application claims the benefit of the filing date of U.S. Provisional Patent Application No. 62/286,671 filed Jan. 25, 2016, the disclosure of which is hereby incorporated herein by reference.

BACKGROUND OF THE INVENTION

Bone fixation procedures often include repositioning displaced bone fragments and holding such fragments in a desired position until permanent fixation means, such as bone plates, threaded fasteners, staples, pins, nails, and the like, can be applied. Clamps or other reduction devices are commonly used to provisionally hold repositioned bone fragments so as to avoid dislocation thereof while the operator applies such fixation means. However, many of the currently available reduction devices are limited to holding only bone fragments which requires the operator to manually position and hold other devices, such as the fixation means, drill guides, and the like, against the bone for use thereof which is time consuming and can potentially result in inadvertent movement of such devices and ultimately misalignment of the fixation means and repaired bone. In addition, many of the currently available reduction devices can obstruct an approach to a fracture site and require the operator to hold the instrument at all times which can limit the other actions the operator can perform.

Therefore, further improved instruments for use in bone fixation procedures are desirable.

BRIEF SUMMARY OF THE INVENTION

Described herein are devices, assemblies, kits and methods for performing bone fixation procedures. In particular, a described bone reduction instrument is configured to hold bone fragments in desired relative positions while simultaneously holding a bone plate/implant adjacent to or against underlying bone for permanent fixation thereof. In addition, the bone reduction instrument is configured so that a pilot hole can be drilled into bone through the instrument and through the bone plate. The instrument is further configured to allow a fastener to be inserted through the instrument to attach the bone plate/implant to the underlying bone. In this regard, a single reduction instrument can be used to perform one or more of the following: hold bone fragments, hold a bone plate/implant adjacent to or against bone, guide a cutting device into bone, and guide a fastener into bone. The instrument may include a removable handle that can facilitate easy grasping by a user, as well as provide a support for resting the device against a static structure, such as a portion of an operating table.

More particularly, in one aspect of the present disclosure, a bone reduction instrument includes first and second members moveably coupled to each other such that ends of the first and second members are positionable in first and second positions. In the second position the first and second members are closer to each other than in the first position. A support member is disposed at the end of the first member and includes an engagement feature configured to hold an implantable device in the first and second positions.

In addition, the engagement feature may be a first opening extending through a body of the support member and defined by one or more wall portions having a conforming geometry configured to engage the implant in a friction-fit manner when disposed within the first opening. The one or more wall portions may include one or more prongs at an end thereof configured to engage bone. The support member may also include a second opening extending therethrough and intersecting the first opening. The second opening may be sized to receive a fastener such that the fastener can be passed entirely through the body and the implantable device. The second opening may be defined by a ring portion and the one or more wall portions may extend downwardly from the ring portion. One or more upwardly extending wall portions may from the ring portion opposite the downwardly extending wall portions. The upwardly extending wall portions may at least partially define the second opening.

Continuing with this aspect, the support member may be rotatably attached to the end of the first member. The ends of the first and second members may be distal ends, and the first and second members may be pivotably joined at a pivot located at proximal ends thereof. The instrument may also include a handle releasably connected to one of the first or second members. The handle may include a head capable of being positioned at various positions.

In another aspect of the present disclosure, a bone fixation kit includes a bone plate having an opening extending therethrough. The also includes a bone reduction instrument having first and second arm members joined together at a pivot such that ends of the first and second arm members are adjustable relative to each other. The first arm member may have a support member at the end thereof. The support member may have a first opening configured to receive a portion of the bone plate in a friction-fit manner.

Moreover, the support member may be rotatably attached to the end of the first arm member. The support member may include a second opening intersecting the first opening such that the second opening communicates with the opening of the bone plate when the bone plate is received by the first opening of the support member. The kit may also include a fastener configured to extend into the opening of the bone plate and fix the bone plate against a portion of a bone. The second opening of the support member may be sized to allow passage of the fastener entirely therethrough and into the opening of the bone plate.

In a further aspect of the present disclosure, a method of bone fixation includes engaging an implant with a first member of a reduction instrument; holding the implant adjacent a first bone fragment via the reduction instrument; holding the first bone fragment against a second bone fragment and between the first member and a second member of the reduction instrument; and inserting a fastener through the end of the first member and into the implant and first bone fragment.

In addition, the method may include supporting the implant in a friction-fit manner at the end of the first member. The method may also include attaching a drill guide to the end of the first member such that an opening of the drill guide is in communication with an opening in the end of the first member; and drilling into the first bone fragment through the opening of the drill guide, the opening of the first member, and an opening in the implant. Moreover, the method may include resting a handle of the reduction instrument against a surface without manual support while the first and second bone fragments are held against each other and the implant is held adjacent to the first bone fragment. Holding the first bone fragment against the second bone fragment may include directly contacting the first bone fragment with the end of the first member, directly or indirectly contacting the second bone fragment with an end of the second member, and clamping the first and second bone fragments therebetween. The implant may be disposed between bone engagement features of the end of the first member. The method may further include the step of rotating the implant with respect to the first member.

In yet another aspect of the present disclosure, a method of holding a bone plate adjacent bone includes connecting a bone plate to a first member of a holding instrument such that the bone plate is supported by the first member without manual support; locating bone between the first member and a second member of the holding instrument while the first and second members are in an unclamped configuration; moving the first and second members toward each other and into a clamped configuration such that first and second arms clamp the bone therebetween and such that the bone plate is placed adjacent to the bone and held in position by the first member; and locking the first and second members in the clamped configuration.

In addition, the connecting step may include inserting a portion of the implant into an opening within an end of the first member sized to form a friction fit with a periphery of the implant. The bone may include a first bone fragment and a second bone fragment, the locating step may include locating the first and second bone fragments between the first and second members, and the moving step may include clamping the first and second bone fragments against each other via the first and second members.

BRIEF DESCRIPTION OF THE DRAWINGS

The features, aspects, and advantages of the present invention will become better understood with regard to the following description, appended claims, and accompanying drawings in which:

FIGS. 4-7A depict a method of fixing a bone plate to bone using the bone reduction instrument of FIG. 1 and a drill guide according to an embodiment of the present disclosure.

FIG. 7B is a cross-sectional view of the distal end of the first arm of the bone reduction instrument of FIG. 1, the implant, the drill guide, and a drill bit in exemplary use as depicted in FIG. 7A.

DETAILED DESCRIPTION

As used herein, when referring to certain directions and orientations of the devices described in the following discussion, it should be understood that such directions and orientations are described in relation to an operator during exemplary application of such devices. Thus, as used herein, the term "proximal" means closer to the operator or in a direction toward the operator, and the term "distal" means more distant from the operator or in a direction away from the operator. Also, as used herein, the terms "about," "generally," and "substantially" are intended to mean that slight deviations from absolute are included within the scope of the term so modified.

FIGS. 1-3C depict a bone reduction/implant holding instrument 10 according to an embodiment of the present disclosure. Instrument 10 is preferably made from a biocompatible material such as stainless steel, titanium, and cobalt-chromium, for example. In addition, instrument 10 may be provided in many different sizes to accommodate different bones. For example, instrument 10, as shown, is sized to accommodate phalanx bones. However, instrument 10 can be sized to accommodate other bones, such as a metacarpal, metatarsal, radius, ulna, and the like.

Instrument 10 generally includes a first arm member 20, a second arm member 30, and a modular handle 70. First arm member 20 (best shown in FIG. 1) is an elongate structure that has a proximal end and a distal end. First arm member 20 curves inferiorly or downwardly at a location near the distal end thereof which delineates first arm member 20 into a proximal portion 22 and a distal portion 24. However, it should be understood that arm member 20 can bend in other directions or not be bent at all. Distal portion 24 extends from proximal portion 22 at an oblique angle.

Figure 1:
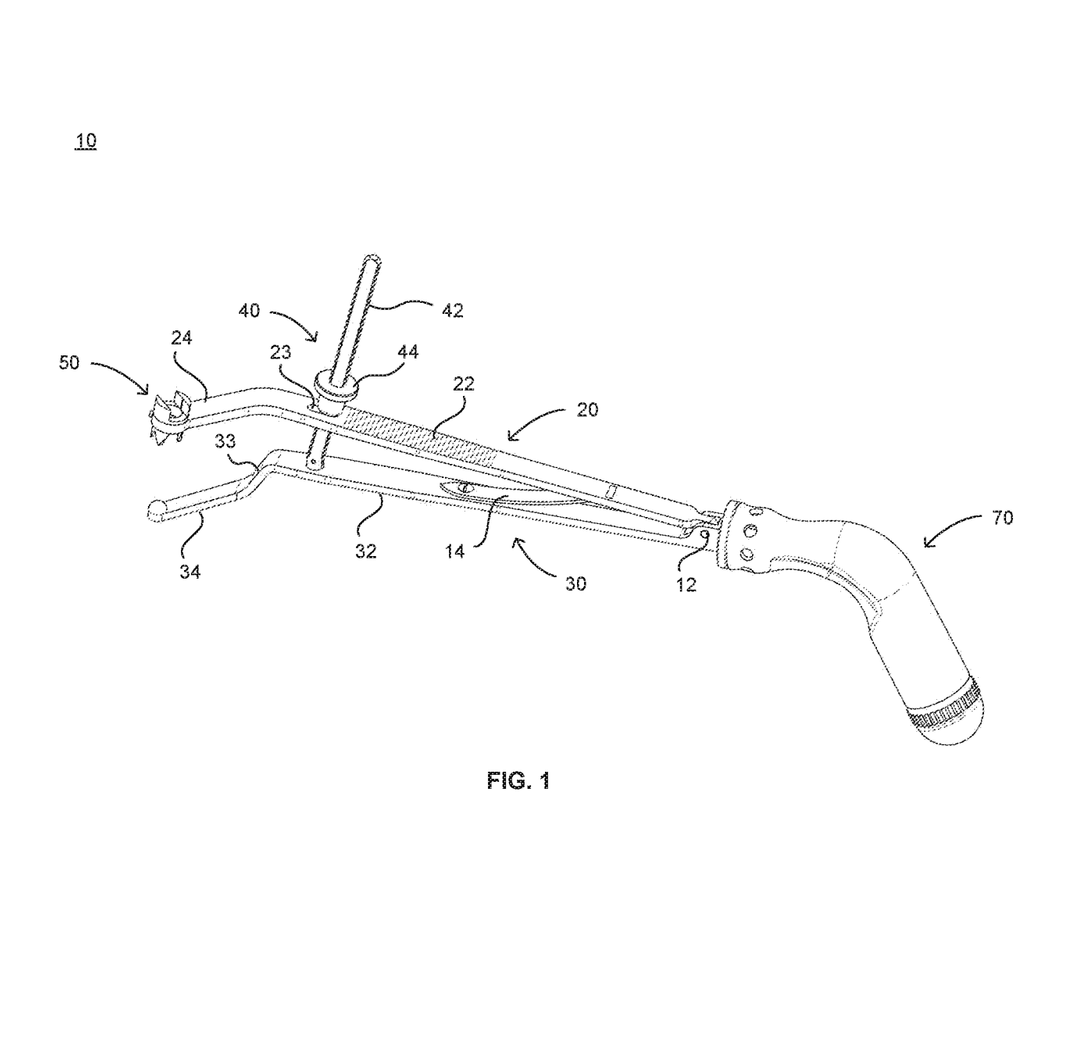
FIG. 1 is a front perspective view of a bone reduction instrument according to one embodiment of the present disclosure

Second arm member 30 is generally an elongate structure that has a proximal end and a distal end. Second arm member 30 curves inferiorly or downwardly at more than one location near the distal end thereof which delineates second arm member 30 into a proximal portion 32, intermediate portion 33, and a distal portion 34. However, it should be understood that arm member 30 can bend in other directions or not be bent at all. Intermediate portion 33 joins proximal and distal portions 32, 34 and forms an angle between proximal portion 32 generally steeper than an angle formed between distal portion 34 and intermediate portion 33.

First arm member 20 and second arm member 30 are pivotably coupled at a pivot 12, such as a pin or bearing, located at their respective proximal ends. A spring 14 is connected to and extends between proximal portions 22, 32. This spring 14 is biased so as to rotate arms 20, 30 about pivot 12 and force distal portions 24, 34 away from each other. Opposing forces applied to arms 20, 30 compressing spring 14 against its normal bias may move distal portions 24, 34 toward or nearer to each other.

Figure 5:
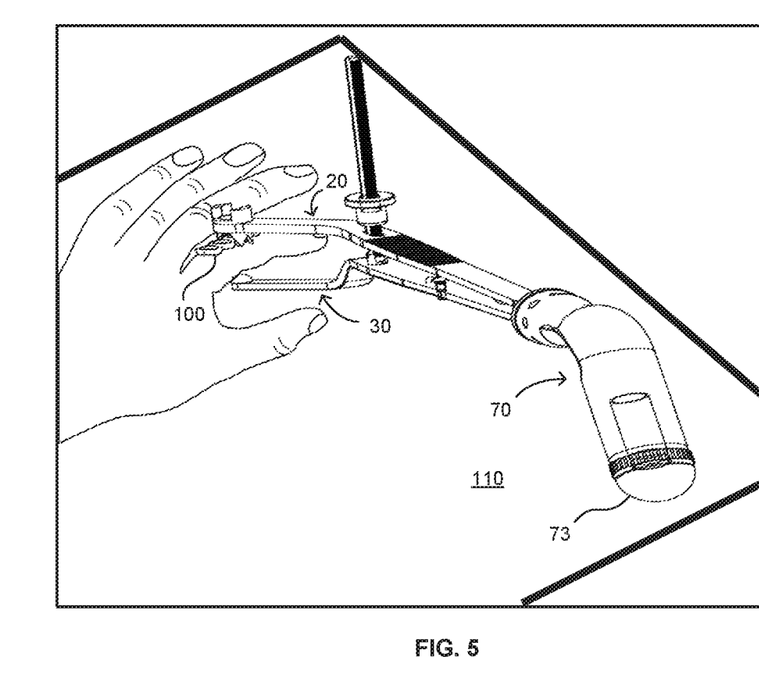

First and second arm members 20, 30 can be locked into a plurality of positions relative to each other by an adjustment mechanism 40. One such position is an unclamped or release position in which distal portions 24, 34 are separated a distance substantially wider than an item disposed therebetween. Another such position is a clamped or holding position in which distal portions 24, 34 are separated a distance sufficiently close to clamp/hold an item or items, such as a bone and/or plate, therebetween. The configurations of the first and second arm members 20, 30 help position distal portions 24, 34 so that they more directly face each other within a typical clamping range and so as to create a space between arms 20, 30 to help visualize an item being clamped, which is best illustrated in FIG. 5. The orientation of the distal and proximal portions of arms 20, 30 also help an operator navigate a patient's anatomy through various different surgical approaches.

Adjustment mechanism 40 includes a threaded post 42 which is pivotably attached to proximal portion 32 of second arm member 30 and extends through a slot 23 in proximal portion 22 of first arm member 20. This allows post 42 to pivot as it is advanced through slot 23 when arm members 20, 30 are moved into various relative positions so as to avoid interfering with such movement. A locking nut 44 threadedly engages post 42 and can abut proximal portion 22 to counteract the bias of spring 14 in order to hold first and second arm members 20, 30 in a desired relative position, such as the clamped or unclamped positions.

While the proximal ends of arm members 20, 30 are pivotably joined together, the distal ends of arm members 20, 30 are configured to clamp and perform other operations to an item or items located therebetween. As best shown in FIGS. 2A-2D, first arm member 20 includes a support/guide member 50 connected to its distal end. Support/guide member 50, as shown, is a sleeve-like structure that is rotatably mounted to distal portion 24 of first arm member 20.

In particular, support/guide member 50 is configured to support and guide an implant, such as the bone plate 100 illustrated in FIGS. 2B-2D, and to support and guide a drill guide and implant fastener (described below). As is best shown in FIGS. 2C-2D, support/guide member 50 includes a ring or annular portion 52, a first end-portion or guide portion 54 and a second end-portion or bone plate retaining portion 56. Ring portion 52 has a groove in an outer surface thereof and extends about a perimeter thereof. As best illustrated in FIG. 2D, ring portion 52 is attached to a collar 26 disposed at the distal end of first arm member 20 such that an inwardly projecting tongue 28 of collar 26 is disposed within the groove of ring portion 52 allowing ring portion 52 to rotate within collar 26 while preventing it from being axially displaced. A press-fit pin 27 extends through collar 26 and abuts ring portion 52 to apply pressure thereto so that ring portion 52 does not freely rotate without deliberate intervention by an operator. In some embodiments, ring portion 52 may have a plurality of detents (not shown) extending thereabout and pin 27 may be spring loaded or otherwise moveable so as to engage the detents to lock ring portion 52 in various angular orientations about a longitudinal axis of support/guide member 50.

First end-portion 54 is comprised of a plurality of wall portions 54a-b extending from ring portion 52 in a generally superior/upward direction as depicted in FIGS. 2C and 2D. However, in some embodiments, first end-portion 54 may be comprised of a single, cylindrical wall as an extension of ring portion 52. The upwardly extending wall portions 54a-b are distributed about ring portion 52 so as to form gaps therebetween. Wall portions 54a-b help stabilize a drill guide (described below) disposed therebetween, and the gaps between wall portions 54a-b help visualize when the drill guide is fully seated.

Second end-portion 56 is comprised of a plurality of wall portions, fingers or flanges 56a-b extending from the ring portion in a generally inferior/downward direction as depicted. Such direction is also in a direction toward second arm member 30. Free ends of the downwardly extending wall portions 56a-b are pointed, wedge-shaped, or otherwise configured to engage bone to prevent movement of support/guide member 50 relative thereto.

A first opening or guide opening 51 extends through a length of guide/support member 50 from first end-portion 54 to second-end portion 56. In addition, a second opening 53 extends through second end-portion 56 in a direction transverse to an axis defined by first opening 51 so that first and second openings 51, 53 intersect and so that second opening 53 forms a passageway or space for receipt of implant 100. The axis defined by first opening 51 is transverse to a longitudinal axis of distal portion 24 of first arm member 20. However, depending on the orientation of support/guide member 50, an axis defined by second opening 53 can be either transverse to or aligned and offset relative to the longitudinal axis of distal portion 24. Thus, for example, as shown in FIG. 2C, implant 100 may be supported or suspended by second end-portion 56 so that a longitudinal axis defined by implant 100 is transverse to distal portion 24 (as shown), or implant 100 may be oriented so that it is aligned but disposed offset from distal portion 24 (not shown).

First and second openings 51, 53 are defined by inner surfaces of support/guide member 50 which are configured to support and suspend implant 100 and to guide and support a drill guide and/or fastener. In particular, the depicted embodiment includes a cylindrical inner surface 55 and first and second tapered inner surfaces 58, 59. Cylindrical inner surface 55 extends from first end-portion 54 to at least ring portion 52 and is sized to receive a portion of a drill guide therein. First tapered inner surface 57 tapers outwardly generally from an interface with cylindrical inner surface 55 toward the free ends of second end-portion 56. An annular shoulder 57 is formed at this interface, which provides a depth stop for a drill guide or some other device. First tapered inner surface 58 is conically tapered to conform to a rounded periphery of implant 100. However, depending on the shape of an implant, first tapered inner surface 57 can have any shape configured to hold the implant in a friction-fit manner. In addition, due to the taper, different sized implants can be inserted into second opening 53 and held therein.

To assist in the holding of the implant within second opening 53, second tapered surface 59 generally tapers inwardly from an interface with first tapered inner surface 58 toward the free ends of wall portions 56a-b, as best shown in FIG. 2D. However, it should be understood that second tapered surface 59 is optionally provided as first tapered surface 58 may be sufficient to provide a friction fit to suspend implant 100 within second opening 53. Downwardly extending wall portions 56a-b may be resiliently flexible such that they may flex outwardly to allow the second opening to receive implant 100 and flex inwardly once implant 100 is positioned beyond the narrowest location of the second tapered surface 59. Thus, as shown in FIGS. 2C and 2D, implant 100 can be held by support/guide member 50 so that first opening 51 thereof is aligned with an opening of implant 100.

Figure 2A:
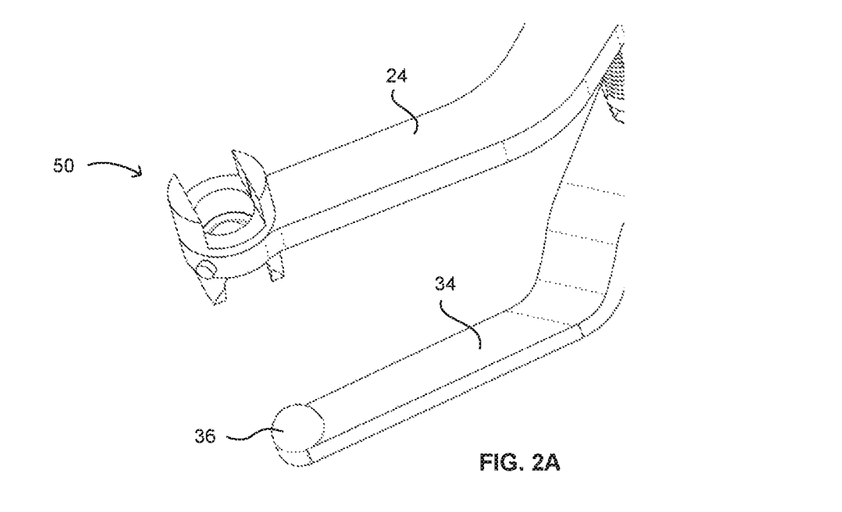
FIG. 2A is an enlarged perspective view a distal end of first and second arms of the instrument of FIG. 1.
Figure 2B:
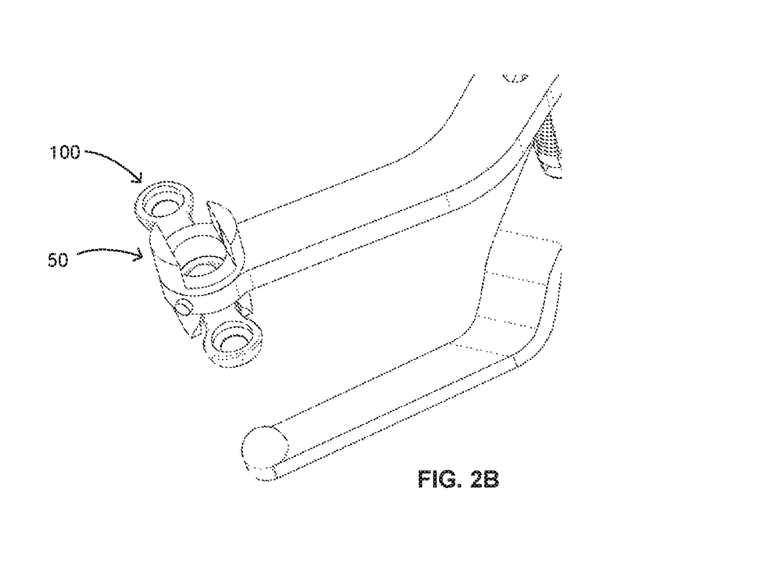
FIG. 2B is an enlarged perspective view of the distal end of the first and second arms instrument of FIG. 1 with a bone plate attached thereto.
Figure 2C:
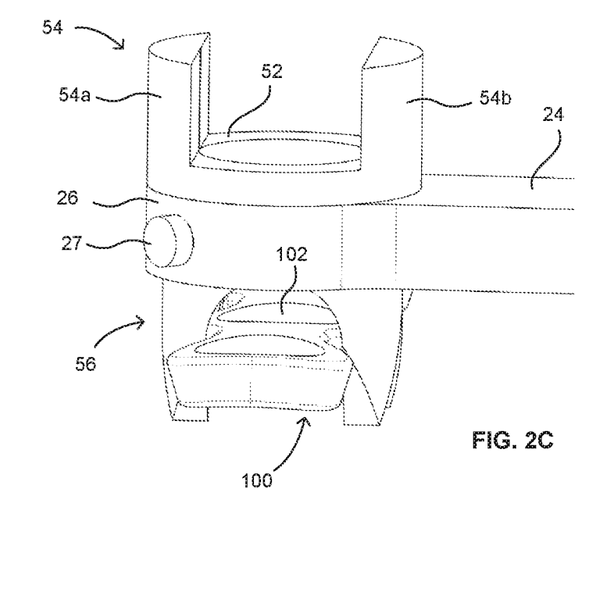
FIG. 2C is an enlarged front view of the distal end of the first arm of the instrument and bone plate of FIG. 2B.
Figure 2D:
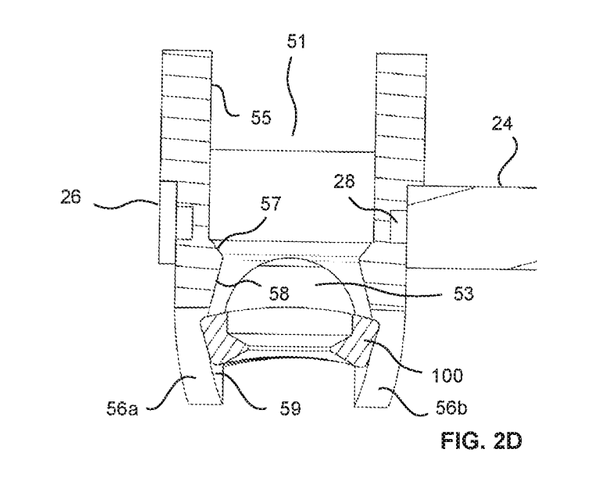
FIG. 2D is cross-sectional view of the distal end of the first arm of the instrument and bone plate of FIG. 2B taken along a midline thereof.

As shown in FIGS. 2A and 2B, the distal end of second arm member 20 includes at least one engagement feature 36 which is configured to contact and engage the outside of a patient's skin or soft tissue. In the embodiment depicted, engagement feature 36 is a domical structure, sphere or spheroid that helps provide a firm purchase against the patient's skin without penetrating it. Although, it is possible to utilize the depicted engagement feature 36 to directly contact bone. Other engagement features for contacting a patient's skin or soft tissue are contemplated and include, for example, a roughed surface; a corrugated surface, and a concave surface configured to partially wrap about a patient's anatomy, such as a finger. In embodiments where engagement feature 36 is meant to contact bone, it could include spikes or other bone penetrating elements that allow for a more solid purchase of the bone.

Figure 3A:
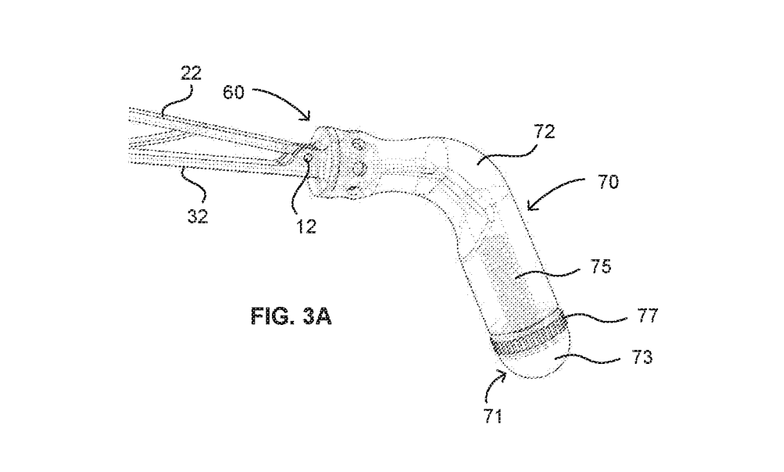
FIG. 3A is an enlarged, partial transparent view of a proximal end of the instrument of FIG. 1 in a first configuration including a modular handle.
Figure 3B:
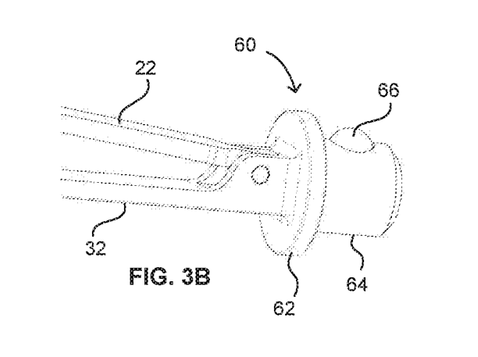
FIG. 3B is an enlarged perspective view of the proximal end of the instrument of FIG. 1 in a second configuration without the modular handle.
Figure 3C:
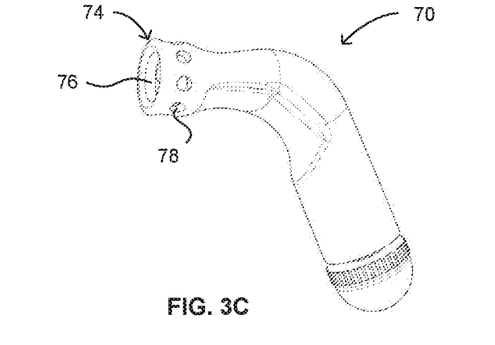
FIG. 3C is perspective view of the modular handle of FIG. 3A.

Referring to FIGS. 3A-3C, modular handle 70 is selectively attachable to a proximal end of arm members 20, 30 via an attachment mechanism. For example, the attachment mechanism may be corresponding threaded connectors. However, in the embodiment depicted, the attachment mechanism is a ball-detent mechanism. In particular, a male connector 60 is provided proximal to pivot 12 and, as shown, is integral with the proximal end of second arm member 32. Male connector 60 includes an end plate 62 and a cylindrical extension 64 extending proximally therefrom. Extension 64 includes a ball 66 disposed in a side surface thereof.

Handle 70 includes a curved body 72 which includes a female connector 74 at one end and an adjustable end member 71 at the other end. Female connector 74 includes an opening 76 for communicating with extension 64 of male connector 60. Opening 76 defines a cylindrical wall that includes a plurality of detents 78 extending therethrough. Detents 78 are disposed about a circumference of handle 70 so that ball 66 can detachably engage detents 78 in multiple handle orientations relative to arm members 20, 30. It is noted that any number of balls and detents may be provided on the structures, and that handle 70 could include the ball(s) while extension 64 includes the detent(s).

Figure 4:
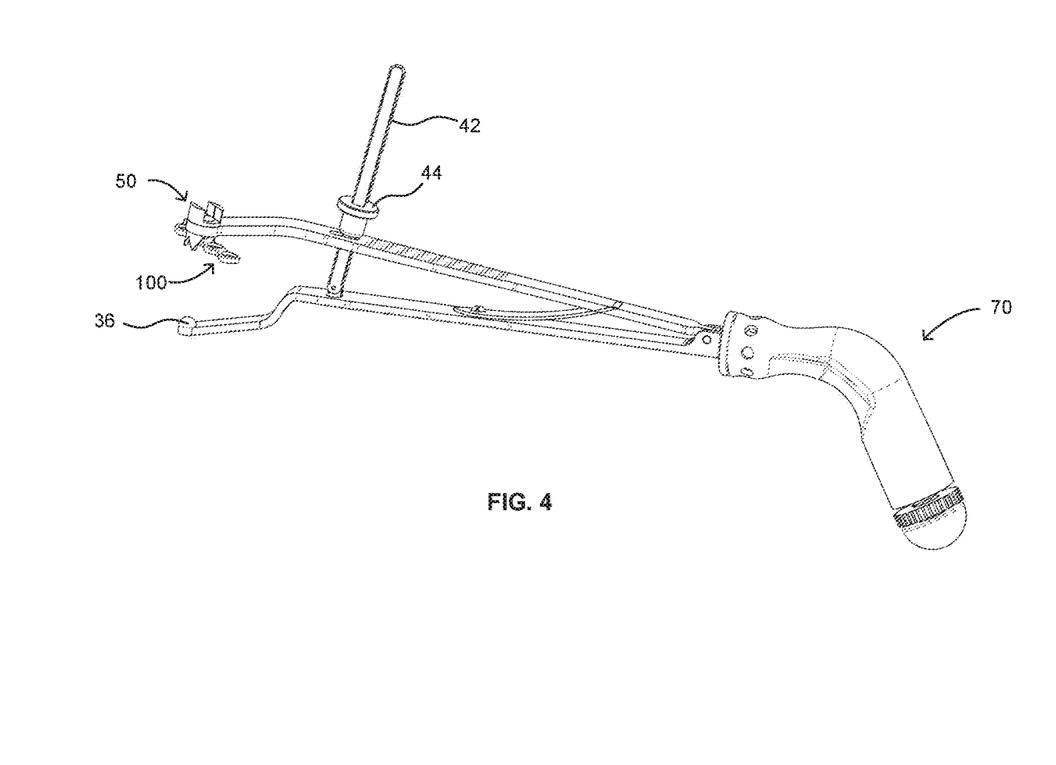

Adjustable end member 71 includes a head 73 and a threaded extension 75 extending therefrom. Threaded extension 75 is threaded to body 72 allowing head 73 to be positioned in multiple positions closer to or farther from body 72. A threaded washer 77 is disposed between head 73 and body 72 to lock head 71 in any one of these multiple positions. FIG. 4 in fact depicts head 73 in an extended position from the remainder of handle 70.

Figure 6:
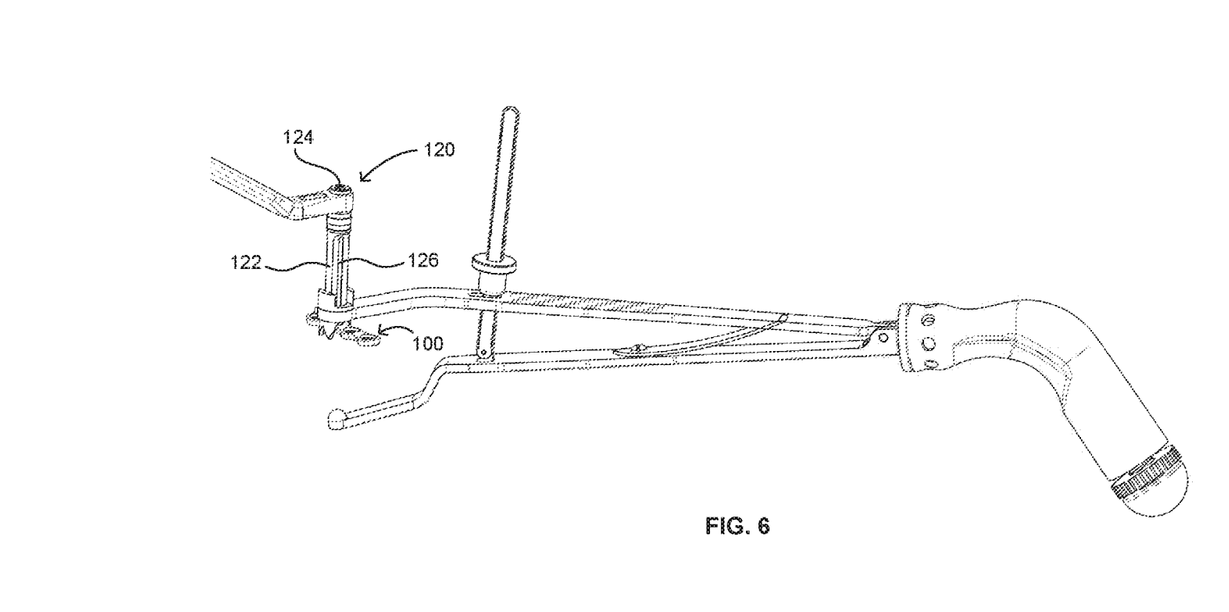
Figures 7A, 7B:
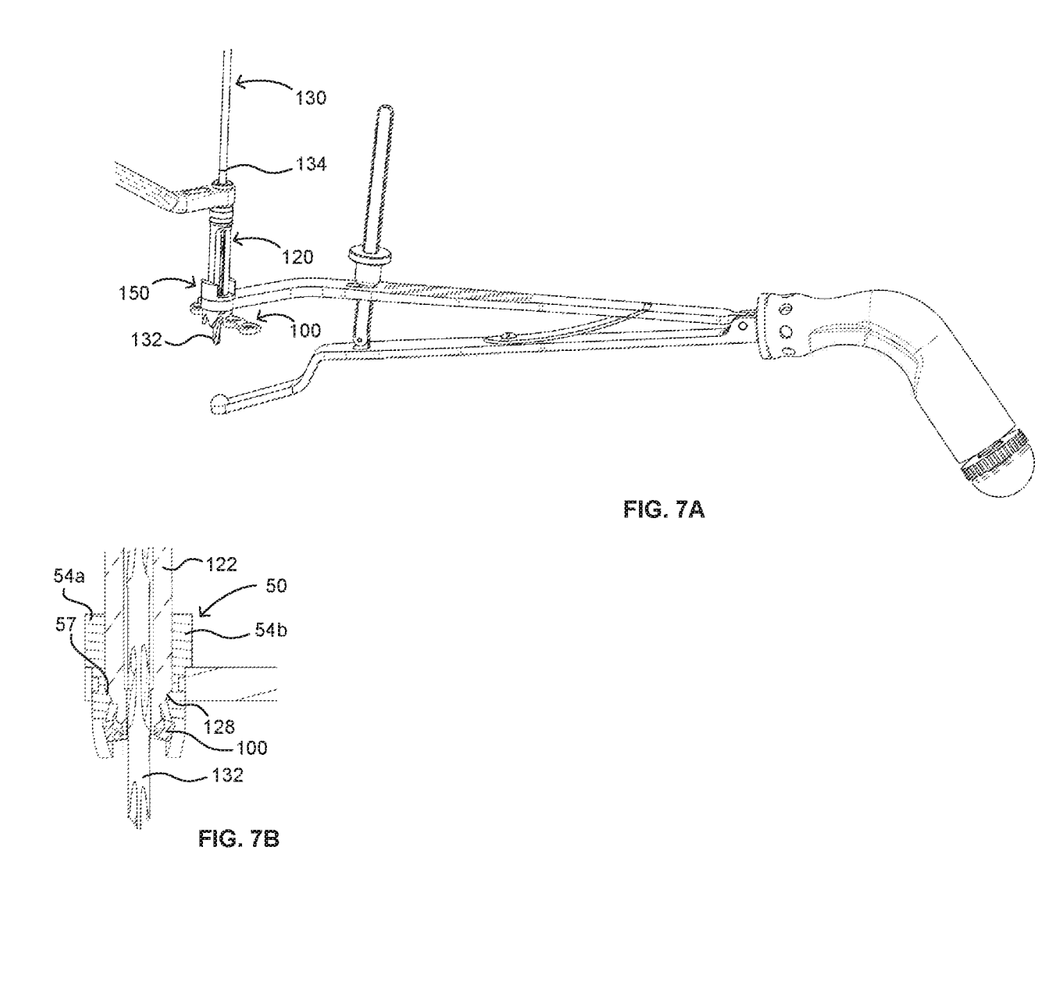

As mentioned above, support/guide member 50 is configured to guide and support a drill guide. One such drill guide embodiment is depicted in FIGS. 6-7B. As depicted, drill guide 120 includes a bearing member 122 that has a cylindrical profile and includes an opening 124 extending through an entirety of its length for receipt of a drill bit 130 therein. Bearing member 122 may include a longitudinal slot 126 extending along a length thereof and communicating with opening 124 so as to allow for the removal of bone particles as drill bit 130 cuts through bone. As illustrated in FIG. 7B, bearing member 122 is sized for receipt within first opening 51 of support/guide member 50 and includes an annular surface 128 configured to engage shoulder 57. When bearing member 122 is received within first opening 51, upwardly extending wall portions extend along a portion of the length of the bearing member 122 to help stabilize bearing member 122 therein to provide a solid drilling platform.

Kits can be provided to an operator that includes some or all of the components described above. For example, in one embodiment, a kit may include instrument 10, drill guide 120, and drill bit 130. In another embodiment, a kit may include instrument 10, drill guide 120, drill bit 130, and implant 100. In a further embodiment, a kit may include instrument 10, drill guide 120, drill bit 130, implant 100, and one or more fastener(s) (not shown) configured to engage and implant 100. In yet a further embodiment, a kit may include instrument 10, implant 100, and one or more self-tapping screw(s) (not shown).

FIGS. 4-7B depict a method of bone fixation using instrument 10 to facilitate implantation of implant 100. In the method, an operator identifies a bone fracture site comprised of a plurality of bone fragments for fixation (a sample of such is shown in FIG. 5, although that figure does not show an incised surgical site as would be the case in an actual use of the components of the present invention). The operator gains access to the bone fracture site via a desired approach. Where a bone plate, such as implant 100, is used for fixation, implant 100 is loaded onto support/guide member 50, as illustrated in FIG. 4. This is preferably performed in the operating theatre. However, it is contemplated that loading may occur at the manufacturing facility such that instrument 10 is preloaded with implant 100 before being delivered to the operating theater. Bone plate 100 is loaded by pushing or otherwise forcing a selected portion of implant 100 into second opening 53 from a location beneath downwardly depending walls 56a-b. As implant 100 is being forced into second opening 53, downwardly depending walls 56a-b may flex outwardly to accommodate implant 100. The operator continues to push implant 100 into second opening 53 and into contact with first tapered surface 58 until first tapered surface 58 creates a friction-fit, thereby locking implant 100 into a suspended configuration. At this point, wall portions 56a-b may have flexed inwardly under their own bias allowing second tapered surface 59 to further help retain implant 100 within second opening 53. Of course, surface 58 provides a stop surface and contact of implant 100 therewith may not be required in all instances for the implant to be captured and held by the device. In addition, first opening 51 is aligned with opening 102 of implant 100. Once implant 100 is supported by support/guide member 50 without manual assistance, operator may manually rotated implant 100 and support/guide member 50 into a desired orientation relative to first arm member 24. Pin 27 helps maintain implant 100 and support/guide member 50 in the desired orientation.

Thereafter, the fracture can be reduced and held in place by instrument 10. In this regard, operator repositions bone fragments, such as a first and second bone fragment, so that they are aligned in a pre-fracture relationship. The bone fragments are then placed between distal portions 24, 34 of first and second arm members 20, 30. First and second arm members 20, 30 are then moved from an unclamped configuration into a clamped configuration (see FIG. 5 for a schematic representation) in which the free ends of downwardly depending walls 56a-b directly engage the first bone fragment and engagement feature 36 of second arm member directly or indirectly (e.g., through soft tissue) engages the second bone fragment so as to clamp the first and second bone fragments in their repositioned locations to prevent them from becoming dislocated. In the clamped configuration, implant 100 is located adjacent bone. In this regard, implant 100 may be suspended slightly above bone via support/guide member 50 such that downwardly depending walls 56a-b span a gap therebetween, or implant 100 may directly contact bone along with the downwardly depending walls 56a-b. This may depend on the thickness of implant 100. However, in either circumstance, implant 100 is generally rigidly held in position between bone and first arm member 20. Locking nut 44 is tightened so as to lock first and second arm members 20, 30 in the clamped configuration.

Once the first and second arm members 20, 30 are firmly clamped to bone, the operator may rest handle 70 on a surface, such as surface 110 of FIG. 5. More particularly, operator may rest handle 70 on surface 100 so that adjustable end member 71 contacts surface 110 and body 72 supports instrument 10 and the bone clamped therewith. This allows operator to free his or her hands for other operations while maintaining the target bone and instrument 10 in a desired orientation. If adjustments are desired, operator may extend or retract adjustable end member 71 by rotating head 73 and washer 77 until head is positioned at the desired distance from body 72. However, if the operator so chooses, handle 70 can be used to manually hold instrument 10 in the desired orientation. Alternative, operator may prefer to remove handle 70 which may be achieved by pulling handle 70 off of male connector 60.

Thereafter, drill guide 120 is attached to guide/support member 50. In this regard, an end of bearing member 122 is inserted into first opening of guide/support member, as shown in FIG. 6. Bearing member 122 is held by guide/support member 50 in a stable position by action of instrument 10 being clamped to bone and via upwardly extending wall portions 54*a-b*.

Once bearing member 122 is firmly seated against shoulder 57 within support/guide member 50 (see FIG. 7B), drill bit 130 is inserted through bearing 122, guide/support member 50, and opening 102 in implant 100 so that it is placed against underlying bone. Drill bit 130 is then used to form a pilot hole in the bone through each of the above referenced features. Once the drill bit 130 penetrates bone, such as the cortical of bone nearer engagement feature 36, the depth of the pilot hole can be measured so as to size for a fastener. This may be achieved by observing indicia 134 located on drill bit 130 relative to a proximal surface of bushing 120.

Thereafter, with instrument 100 remaining clamped to bone, drill bit 130 and drill guide 120 are removed from support/guide member 50. A fastener, such as a bone screw, is then inserted through first opening and into implant 100 and the pilot hole. As the fastener is threaded into the bone, implant 100 is pulled by the fastener through second end-portion 56 so that it is no longer independently supported by first arm member 20. Additional fasteners can be inserted into implant if desired. Instrument 10 is released by rotating locking nut 44 so that spring 14 pushes arm members 20, 30 apart and into the release position which leaves implant attached to bone in the position it was originally placed in by instrument 10.

In another method embodiment of the disclosure, instrument 10 is utilized to apply a fastener, such as a lag screw, independent of application of implant 100 to bone and is also utilized in the same procedure to apply implant 100 to the bone via another fastener. Such method is demonstrative of the versatility of instrument 10 to perform multiple operations that may traditionally be performed by multiple instruments. In the alternative method, an operator identifies a bone fracture site comprised of a plurality of bone fragments for fixation. The operator gains access to the bone fracture site via a desired approach. Thereafter, the fracture can be reduced and held in place by instrument 10. In this regard, operator repositions bone fragments, such as a first and second bone fragment, so that they are aligned in a pre-fracture relationship. The bone fragments are then placed between distal portions 24, 34 of first and second arm members 20, 30. First and second arm members 20, 30 are then moved from an unclamped configuration into a clamped configuration in which the free ends of downwardly depending walls 26*a-b* directly engage the first bone fragment and engagement feature 36 of second arm member 30 directly or indirectly (e.g., through soft tissue) engages the second bone fragment so as to clamp the first and second bone fragments in their repositioned locations to prevent them from becoming dislocated. It is noted, that no implant is attached to instrument 100 at this point in the method.

Thereafter, drill guide 120 is attached to guide/support member as previously described and drill bit 130 is inserted through drill guide 120 and support/guide member 50. A pilot hole is drilled into bone which may extend through the first and second bone fragments and span across a fracture. Drill guide 120 is then removed from instrument 10 and a first fastener, such as a lag screw, is inserted through support/guide member 50 into the pilot hole which secures the bone fragments to each other. Where additional fixation is desired, implant 100 may then be applied by instrument 10 in the same manner described above in relation to the previously described method. In this regard, implant may be fixed by a second fastener applied to the bone at a location offset from the first fastener.

Figure 8:
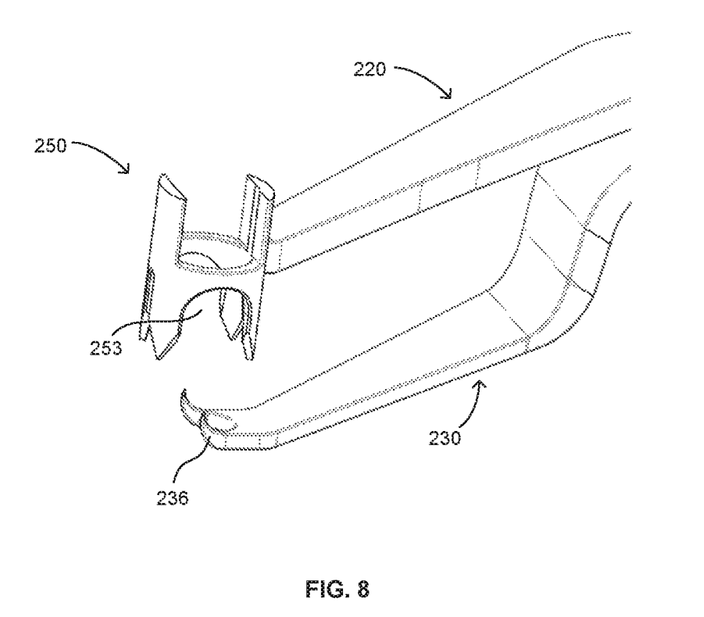
FIG. 8 is an enlarged perspective view of a distal end of first and second arm members of a bone reduction instrument according to another embodiment of the present disclosure.

Numerous variations, additions, and combinations of the features discussed above can be utilized without departing from the present invention. For example, FIG. 8 depicts alternative first and second arm members 220, 230. First arm member 220 is similar to first arm member 20 with one difference being the support/guide member 250 connected thereto. Support/guide member 250 is rigidly connected to the distal end of first arm member 220. In other words, support/guide member 250 does not rotate relative to first arm member 220 as does support/guide member 50. Thus, a second opening 253 of support 250, which may also be configured to secure implant 100 in a press-fit manner therein, may be oriented in a predetermined orientation relative to an axis of first arm member 220 so that an implant, such as implant 100, can be similarly oriented when supported by support/guide member 250.

In addition, second arm member 230, as shown, is similar to second arm member 30 with one difference being the engagement feature 236 disposed at a distal end thereof. For example, as shown in FIG. 8, engagement feature 236 may be specifically configured to engage bone rather than soft tissue. In this regard, engagement feature 236 may include one or more prongs capable of biting into bone to provide a non-slip grip. Other embodiments for directly gripping bone may include roughened or corrugated surfaces, for example. Although engagement feature 236 is shown in FIG. 8 in conjunction with fixed support/guide member 250, it should be understood that engagement feature 236 can be provided on an instrument in conjunction with support/guide member 50, and engagement feature 36 can be provide on an instrument in conjunction with support/guide member 250.

In other bone reduction/holding instrument embodiments, first and second arm members 20, 30 may be pivotably connected at a location along their respective lengths rather than at their proximal ends as described in relation to instrument 10. In other words, pivot 12 may be located between the proximal and distal ends of first and second arm members 20, 30 so that first and second arm members 20, 30 are configured to operate or move relative to one another like a pair of scissors or forceps. In addition, in lieu of adjustment member 40 described above, a ratchet mechanism can be provided to hold arm members 20, 30 in position.

In still further reduction/holding instrument embodiments, an alternative support/guide member (not shown) may be configured to assist in implanting other fixation means, such as staples, to bone. For example, a first opening, such as first opening 51, may be configured in the shape of a staple so that a staple can be inserted through such opening and impacted into bone across a bone fracture. Also, while a friction-fit connection between implant 100 and support/guide member 50 is described above, other support/guide member embodiments can include alternative support/holding means for holding an implant which may include, but are not limited to, manually operable jaws (e.g., threaded jaws), mechanically biased jaws (e.g., spring loaded jaws), snap-fit features, and the like.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A bone reduction instrument, comprising:
   first and second members moveably coupled to each other such that ends of the first and second members are positionable in first and second positions, wherein in the second position the first and second members are closer to each other than in the first position; and
   a support member disposed at the end of the first member and having a plate retaining portion extending from the first member in a direction toward the second member, the plate retaining portion having wall portions that define a space therebetween configured to receive a bone plate so that the bone plate is held between the wall portions when the bone plate is disposed within the space, the wall portions having a conforming geometry configured to engage a periphery of the bone plate in a friction-fit manner.

2. The instrument of claim 1, wherein the wall portions include one or more prongs at an end thereof configured to engage bone to prohibit movement of the support member relative to the bone when so engaged.

3. The instrument of claim 1, wherein the wall portions at least partially define a guide opening that extends through the first member and the support member, the guide opening being sized to allow a bone fastener to pass therethrough and into an opening in the bone plate.

4. The instrument of claim 3, wherein the support member further includes a ring portion that connects to the first member in a rotatable fashion, the wall portions extending from the ring portion.

5. The instrument of claim 4, wherein the support member further includes a guide portion extending from the ring portion in a direction away from the second member.

6. The instrument of claim 1, wherein the support member is rotatably attached to the end of the first member.

7. The instrument of claim 1, wherein the ends of the first and second members are distal ends, and the first and second members are pivotably joined at a pivot located at proximal ends thereof.

8. The instrument of claim 1, further comprising a handle releasably connected to one of the first or second members.

9. A bone reduction instrument, comprising:
   first and second arm members joined together at a pivot such that ends of the first and second arm members are adjustable relative to each other, the first arm member having a support member at the end thereof, the support member having a plate retaining portion extending from the first arm member in a direction toward the second arm member, the plate retaining portion having opposed sidewalls defining a space therebetween sized to receive at least a portion of a bone plate and having a conforming geometry so that the opposed sidewalls of the retaining portion engage the outer periphery of the bone plate in a friction-fit manner.

10. The kit of claim 9, wherein the support member is rotatably attached to the end of the first arm member.

11. The instrument of claim 9, wherein the sidewalls include one or more prongs at an end thereof configured to engage bone to prohibit movement of the support member relative to the bone when so engaged.

12. The instrument of claim 11, wherein the sidewalls at least partially define a guide opening that extends through the first member and the support member, the guide opening being sized to allow a bone fastener to pass therethrough and into an opening in the bone plate.

13. The instrument of claim 12, wherein the support member further includes a ring portion that connects to the first member in a rotatable fashion, the sidewalls extending from the ring portion.

14. The instrument of claim 13, wherein the support member further includes a guide portion extending from the ring portion in a direction away from the second member.

* * * * *